(12) United States Patent
Schwieker

(10) Patent No.: US 6,659,641 B2
(45) Date of Patent: Dec. 9, 2003

(54) X-RAY SYSTEM HAVING A MOVEABLE CARRIER ATTACHED TO A PATIENT TABLE

(75) Inventor: Horst-Hartwig Schwieker, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 171 days.

(21) Appl. No.: 09/968,993

(22) Filed: Oct. 2, 2001

(65) Prior Publication Data

US 2002/0051517 A1 May 2, 2002

(30) Foreign Application Priority Data

Oct. 6, 2000 (DE) .......................... 100 49 538

(51) Int. Cl.⁷ ............................................. H05G 1/02
(52) U.S. Cl. ..................................................... 378/196
(58) Field of Search ............................. 378/21, 25–27, 378/181, 177, 179, 193, 195, 196, 197, 198

(56) References Cited

U.S. PATENT DOCUMENTS

| | | | | |
|---|---|---|---|---|
| 3,852,611 A | * | 12/1974 | Cesar ........................... 378/27 |
| 4,150,297 A | * | 4/1979 | Borggren ..................... 378/181 |
| 4,426,725 A | * | 1/1984 | Grady .......................... 378/196 |
| 4,918,716 A | * | 4/1990 | Hahn ........................... 378/197 |
| 5,044,354 A | * | 9/1991 | Goldhorn et al. .............. 601/4 |
| 5,329,926 A | * | 7/1994 | Herrmann et al. .......... 600/427 |

* cited by examiner

Primary Examiner—William Oen
(74) Attorney, Agent, or Firm—John Vodopia

(57) ABSTRACT

The X-ray system includes a patient table (1, 2, 3) and a radiation module with a radiation source (6) and a radiation receiver (7) and can be universally used for the examination of a plurality of organs by means of a wide variety of methods. Therefore, it is particularly suitable for use in conjunction with one of the novel digital flat detectors which can thus be economically used despite their high price. This is achieved essentially in that the radiation module includes a carrier (4, 5, 51 to 55) on which the X-ray source (6) and the radiation receiver (7) are mounted so as to face one another and which is attached to the patient table so as to be pivotable in such a manner that the X-ray system can be used in the overtable technique as well as in the undertable technique.

10 Claims, 1 Drawing Sheet

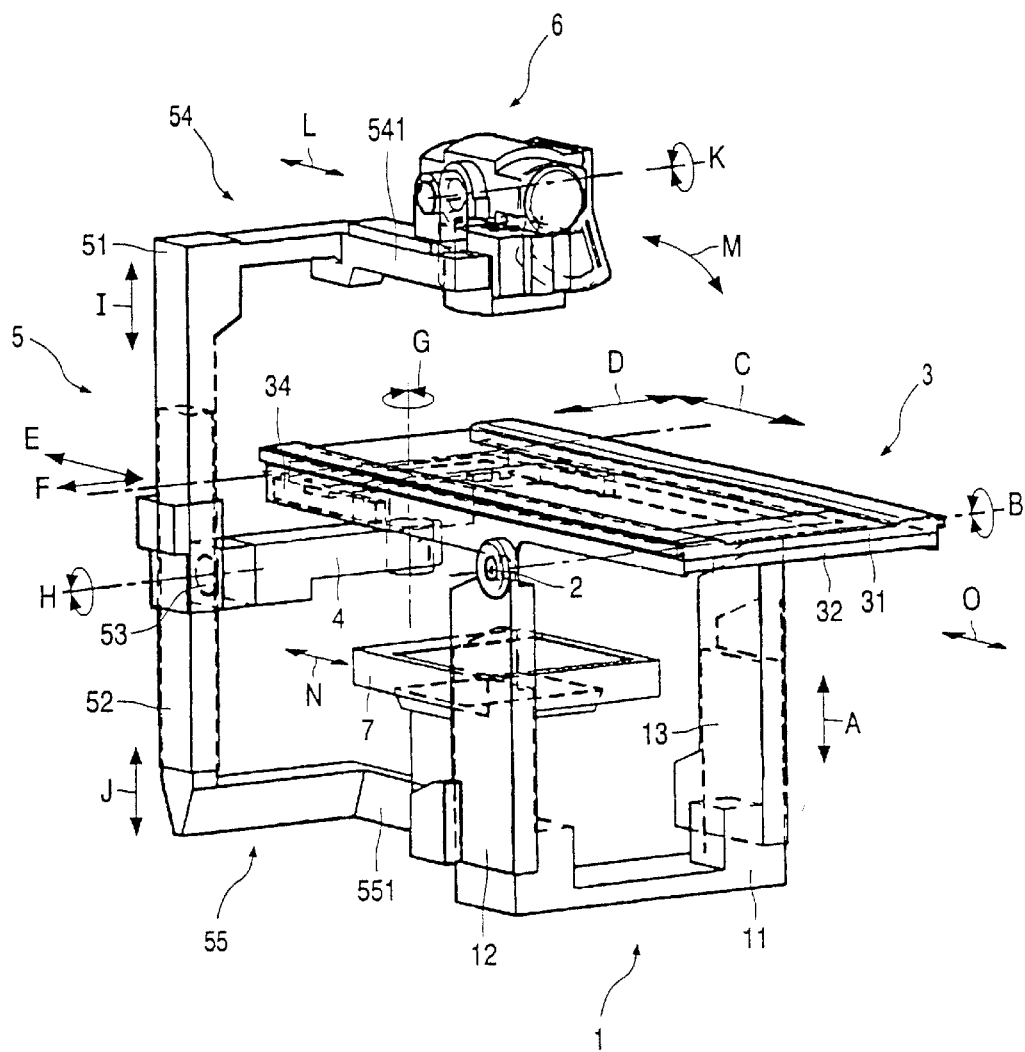

X-RAY SYSTEM HAVING A MOVEABLE CARRIER ATTACHED TO A PATIENT TABLE

FIELD OF THE INVENTION

The invention relates to an X-ray system which includes a patient table and a radiation module with an X-ray source and radiation receiver and serves to form an X-ray image of a patient.

BACKGROUND OF THE INVENTION

It is known that practically any organ of a patient can be subjected to an X-ray examination. A variety of methods are known for this purpose; such methods also include, for example tomography, peripheral and stationary angiography, phlebography etc. A distinction is also made between the acquisition of single images and the imaging of motion, that is, the formation of coherent image sequences. This wide variety of possibilities is reflected in a corresponding wide variety of X-ray systems which are conceived in general, or preferably, for a respective one of these types of examination. Depending on the type of examination, a patient posture or position that is suitable for the imaging of the organ to be examined must be realized by means of the patient table, and it must also be possible to move the radiation module to the corresponding image acquisition position. Finally, the radiation module must also be suitable for the type of image acquisition.

Because, generally speaking, all types of X-ray examinations must be carried out in hospitals, different X-ray systems are required; such systems represent a significant cost factor.

The problem is worsened by the fact that the costs of the X-ray systems are increased further by the deployment of novel digital flat detectors which are comparatively expensive but offer significant advantages because of their compactness and (digital) image processing which is simpler than in the case of conventional image converters.

Therefore, it is an object of the invention to provide an X-ray system of the kind set forth which can be universally used for a significantly larger number of different X-ray examinations.

It is a further object of the invention to facilitate the desired application of new flat detectors or R&F (radiography & fluoroscopy) digital systems by providing an X-ray system which can operate very economically despite the high costs of such detectors.

SUMMARY OF THE INVENTION

The above objects are achieved by means of an X-ray system which includes a patient table and a radiation module with an X-ray source and a radiation receiver, the radiation module including a carrier which is attached to the patient table and on which the X-ray source and the radiation receiver are mounted so as to face one another, said carrier being pivotable in such a manner that the X-ray source and the X-ray receiver can be moved from a position over and under a top of the patient table ("overtable technique") to a reversed position under and over the table top, respectively ("undertable technique").

This solution has a special advantage in that the X-ray system in accordance with the invention can be simply adjusted in conformity with the type of organ to be imaged and with the examination to be carried out, and hence can be universally used for a number of different examinations which is significantly larger than the number enabled by known system; for example, image exposures involving oblique irradiation are also possible.

The dependent claims relate to advantageous further embodiments of the invention.

The embodiments in accordance with the claims 2 and 3 offer the advantage of a compact structural unit which can be comparatively simply assembled and adjusted.

The embodiments in accordance with the claims 5 and 6 further enhance the adjustability of the X-ray source and the X-ray receiver. A spectrum of applications which includes practically any type of X-ray examination is achieved notably in combination with the adjustability of the patient table as achieved by the embodiments disclosed in the claims 4, 8 and 9.

Finally, the embodiment in accordance with claim 7 enables separate, optimum adjustment of the X-ray source and the radiation receiver, notably in the case of lateral examinations.

BRIEF DESCRIPTION OF THE DRAWINGS

Further details, characteristics and advantages of the invention will become apparent from the following description of a preferred embodiment which is given with reference to the drawing. Therein:

FIG. 1 is a three-dimensional diagrammatic view of an X-ray system in accordance with the invention.

DETAILED DESCRIPTION OF THE PREFERRED EMBODIMENTS

The X-ray system in accordance with the invention consists of a patient table and a radiation module.

The patient table includes an essentially U-shaped frame 1 with a base 11 and two lateral braces 12, 13 which extend upwards. The two braces are telescopically extendable in conformity with the arrow A, thus enabling adjustment of the height of the frame 1, for example, in a range of between approximately 740 and 1220 mm.

At the two upper ends of the lateral braces 12, 13 a table top 3 is journaled by way of a pivot 2 (only one of which is shown) so as to be pivotable. The dimensions are chosen to be such that from the horizontal position as shown in FIG. 1 the table top can be tilted approximately 90 degrees forwards and up to approximately 45 degrees backwards about a horizontal first axis (arrow B) which extends perpendicularly to the longitudinal direction of the table top. The table top 3 includes a supporting plate 31 for supporting a patient and a frame 32 on which the supporting plate 31 is guided in such a manner that it can be shifted approximately +/−300 mm in the longitudinal direction (arrow C) and approximately +/−80 mm in the transverse direction (arrow D). A carriage 34 (denoted by dashed lines) is guided on the frame 32; the radiation module is mounted on said carriage which can be displaced approximately from 400 to 700 mm in the longitudinal direction of the table top 3, that is, as denoted by the arrow E.

The radiation module includes a pivotable carrier 4, 5; an X-ray source 6 and a radiation receiver 7 (for example, an image intensifier or a digital flat detector with an anti-scatter grid) are mounted at the opposite ends of said carrier. The carrier includes a first arm 4 which extends essentially parallel to the plane of the table top 3 and a first end of which is journaled on the carriage 34 in such a manner that it (and hence the entire radiation module) can be displaced approximately from 160 to 320 mm in the transverse direction of the table top 3, that is, as denoted by the arrow F. Because of the mobility of the carriage 34 in the longitudinal direction of the table top 3, the entire radiation module can also be displaced in this direction (arrow E).

The first end of the first arm 4, furthermore, is journaled on the carriage 34 so as to be pivotable, in accordance with the arrow G, about a second axis which is perpendicular to the table top 3, in such a manner that it can be pivoted through an angle of approximately 180 degrees to the right from the position shown in FIG. 1.

A second arm 5 (shown to extend vertically in FIG. 1) is pivotably attached to the second end of the first arm 4, by way of a pivot 53; this second arm extends essentially in a plane perpendicular to the plane of the table top and can be pivoted through an angle of approximately +/−180 degrees about the longitudinal axis (third axis) of the first arm 4 in conformity with the arrow H, that is, in a plane extending perpendicularly to the plane of the table top 3.

The second arm 5 includes a first, upper section 51, being shown at the top in the rendition of FIG. 1, a second, lower section 52, as well as the pivot 53 on which the two sections are mounted, guided and configured in such a manner that they can be telescopically moved one into the other in their longitudinal direction as denoted by the arrows I and J. The first section 51 can preferably be moved out up to a length of approximately 800 mm and the second section 52 up to a length of approximately 600 mm, that is, relative to the pivot 53.

This construction of the X-ray system is suitable for operation while using the so-called overtable technique and the so-called undertable technique. This means that the X-ray source 6 can be pivoted from the position over the table 3 and the radiation receiver 7 can be pivoted from the position under the table 3 ("overtable technique") to the respective reverse positions by pivoting the first arm 4 through 90 degrees and the second arm 5 through 180 degrees, that is, to the positions under the table and over the table, respectively (undertable technique). This also enables the formation of oblique images where oblique irradiation of the zone to be examined is performed by pivoting the second arm 5 through a few degrees. Furthermore, free exposures adjacent the table can also be performed by appropriate pivoting of the two arms.

The end of the first section 51 of the second arm 5 which is shown at the top in FIG. 1 is adjoined by an essentially L-shaped first carrier section 54 which is situated in a plane extending essentially parallel to the third axis (in conformity with the arrow H). The X-ray source 6 is guided so as to be slidable along a free limb 541 of this first carrier section 54, that is, in the direction of the arrow L. The X-ray source 6, moreover, is mounted so as to be pivotable in such a manner that it can be pivoted (in conformity with the arrow K) about a fourth axis which extends parallel to the third axis, that is, at an angle of, for example, approximately +/−18 degrees.

Finally, a collimator of the X-ray source 6 can be pivoted about the axis of a central ray of the X-ray source in conformity with the arrow M, that is, at an angle of approximately +/−45 degrees. Consequently, the zone irradiated by the X-ray beam can be rotated or its shape can be varied in such a manner that dedicated irradiation of exclusively the zone to be examined is possible while all other zones are masked.

To the end of the second section 52 of the second arm 5 which is shown at the bottom in FIG. 1 there is attached an essentially L-shaped second carrier section 55 which also extends in a plane that is essentially parallel to the third axis. The radiation receiver 7 is mounted on a free limb 551 of said second carrier section 55, said radiation receiver being slidable along said limb, that is, in the direction of the arrow N. The L-shaped carrier sections 54, 55 also enable tomographic images to be acquired ("layer imaging technique") when the X-ray source 6 is displaced in one direction in conformity with the arrow L and the radiation receiver 7 is in conformity with the arrow N in an opposite direction while the X-ray source 6 is pivoted at the same time about the fourth axis in conformity with the arrow K, so that it always remains aimed at the radiation receiver.

The L-shaped carrier sections 54, 55 also enable the formation of optimum lateral images ("lateral table technique"), that is, images in the transverse direction across the table, in that starting from the position of the radiation module that is shown in FIG. 1, first the arm 4 is pivoted 90 degrees to the right (at the rear) and subsequently the second arm 5 is pivoted 90 degrees clockwise. The height of the radiation cone over the table can then be adjusted by displacement of the X-ray source 6 as well as of the radiation receiver 7 along the respective free limb 541, 551.

Finally, in known manner a Bucky module (grid drawer) may be provided as a further radiation receiver (not shown) underneath the table top; this module can be displaced in the direction of the arrow O and be used in known manner for the acquisition of photographic single images.

All motions of the X-ray system that have been described with reference to the arrows A to O are preferably realized out by means of appropriate electric motors and drive units.

This geometry and the described adjustment facilities create, because of their nature and their scope, a universal X-ray system which is suitable for the examination of practically all organs by means of the widest variety of methods, for example, also in urology and lithotripsy.

Moreover, the system is suitable for the acquisition of photographic single images by means of the Bucky module that is guided underneath the table top 3, as well as for the acquisition of dynamic images, that is, moving images. The radiation receiver 7 that is arranged on the second carrier section 55 of the second arm 5 is either a known image converter or a digital flat detector or a digital system intended for radiology and fluoroscopy (R&F). Because the flat detectors are also suitable for the acquisition of up to several images per second, they are particularly advantageously used in the X-ray system in accordance with the invention, so that the Bucky module can be dispensed with. Because of the universal usability of such a system, the comparatively high price of such detectors is no longer as decisive a cost factor as before.

A further advantage of the X-ray system in accordance with the invention results from the fact that it has a modular construction and that it can operate in different stages of assembly in conformity with the building brick principle. In its simplest version the X-ray system is used, for example for urological examinations. In that case it is only necessary to adjust the height of the table top 3 vertically in conformity with the arrow A and to pivot the table top in conformity with the arrow B; for the radiation module it is only necessary to perform the motion of the first arm 4 in the longitudinal direction and the transverse direction of the table in conformity with the arrows E and F.

In a somewhat extended version for urological examinations, for example, the Bucky module is arranged underneath the table top 3 and the supporting plate 31 is displaceable on the frame 32 in the longitudinal direction and the transverse direction in conformity with the arrows C and D.

When examinations for lithotripsy are to be carried out at the same time by means of the X-ray system, pivoting of the second arm 5 about the third axis in conformity with the arrow H, displacement of the X-ray source 6 in conformity with the arrow I and displacement of the radiation receiver 7 in conformity with the arrow J are additionally necessary. For this application the top plate 31 is preferably arranged on the frame 32 so as to be slidable in the longitudinal direction and the transverse direction, thus enabling the patient to be positioned accordingly.

In the completely assembled configuration construction shown in FIG. 1, the longitudinal displacement of the X-ray source 6 in conformity with the arrow L and the tilting of the X-ray source 6 about the fourth axis in conformity with the arrow K and the longitudinal displacement of the radiation receiver 7 in conformity with the arrow N enable the X-ray system to be used as a chest stand.

The modular nature of the radiation module and the patient table also enables adaptation of the X-ray system to a range of applications extended at a later stage, for example, by adding or exchanging at a later stage individual components or a plurality of components required for the described movements.

I claim:

1. An X-ray system comprising a patient table and a radiation module with an X-ray source and a radiation receiver, characterized in that the radiation module includes a carrier (4, 5, 51 to 55) which is attached to the patient table (1, 3) and on which the X-ray source (6) and the radiation receiver (7) are mounted so as to face one another, said carrier being pivotable in such a manner that the X-ray source (6) and the radiation receiver (7) can be moved from a position over and under a top (3) of the patient table, respectively, to a reversed position under and over the table top (3), respectively, said carrier further being in operative communication with the patient table (1, 3) such that movement of the carrier along a longitudinal direction of the table top (3) causes movement of the carrier through the patient table (1, 3).

2. An X-ray system as claimed in claim 1, characterized in that the pivotable carrier includes a first arm (4), a first end of which is attached to a frame (32) of the table top (3) in such a manner that it can be pivoted about a second axis which extends essentially perpendicularly thereto.

3. An X-ray system as claimed in claim 2, characterized in that a second arm (5) is attached to the second end of the first arm (4) by way of a pivot (53), said second arm carrying the X-ray source (6) and the radiation receiver (7) and being pivotable in a plane which extends essentially perpendicularly to the plane of the table top (3).

4. An X-ray system as claimed in claim 1, characterized in that the table top (3) is journaled on a frame 1 so as to be tiltable about a first axis, extending in its transverse direction, by way of a pivot (2).

5. An X-ray system as claimed in claim 2, characterized in that a carriage (34) is mounted on the frame (32) of the table top (3) so as to be slidable in the longitudinal direction thereof, the first arm (4) being journaled on said carriage (34) so as to be slidable in the transverse direction of the table top.

6. An X-ray system as claimed in claim 3, characterized in that the second arm (5) is composed of a first section (51) and a second section (52), said sections being mounted on the pivot (53) in such a manner that they can be moved telescopically one in the other.

7. An X-ray system as claimed in claim 6, characterized in that at opposite ends of the first and the second section (51, 52) on the pivot (53) there is arranged a first, essentially L-shaped carrier section and a second, essentially L-shaped carrier section (54, 55), each of said sections being situated in a plane which is essentially perpendicular to the second arm (5), the X-ray source (6) and the radiation receiver (7) being mounted so as to be slidable along a respective free limb (541, 551) of the carrier sections.

8. An X-ray system as claimed in claim 4, characterized in that the table top (3) includes a supporting plate (31) and a frame (32), the supporting plate (31) being mounted on the frame (32) in such a manner that it is displaceable in the longitudinal direction and the transverse direction.

9. An X-ray system as claimed in claim 4, characterized in that the height of the frame (1) is adjustable.

10. An X-ray system as claimed in claim 1, characterized in that the radiation module and the patient table have a modular construction.

* * * * *